March 12, 1968 L. ARENDS Plant Pat. 2,800
APPLE TREE
Filed Nov. 14, 1966
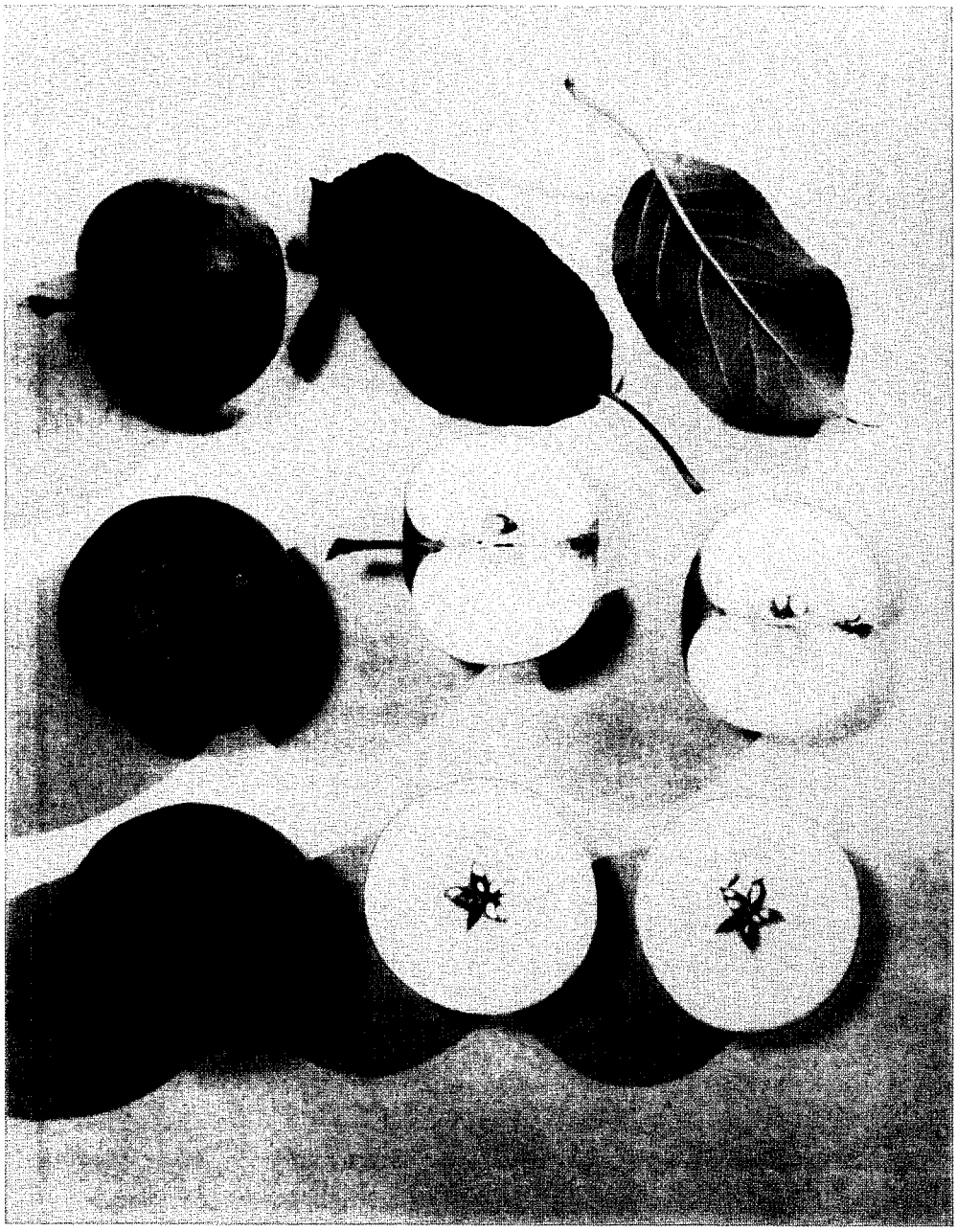
Inventor.
Lewis Arends
By: Robb & Robb
Attorneys.

United States Patent Office

Plant Pat. 2,800
Patented Mar. 12, 1968

2,800
APPLE TREE

Lewis Arends, Sparta, Mich., assignor to Hill Top Orchards and Nurseries, Inc., Hartford, Mich., a corporation of Michigan Filed Nov. 14, 1966, Ser. No. 594,283
1 Claim. (Cl. Plt.—34)

The present invention relates to a new and distinct variety of apple tree which was discovered by me as a newly found seedling of unknown parentage, in a ravine at the back of my farm located in Sparta Township, Kent County, Mich.

Over the years, this ravine referred to above had been used for a cull apple dump, and many seedling trees rooted and grew up in this dump. My new seedling described herein was one of several to which my attention was attracted, but my attraction was particularly drawn to this new seedling by reason of the fact that it bore fruit which ripened considerably earlier than the well known variety "McIntosh" which was being grown extensively in the area of my farm, and by the further outstanding fact that its foliage and fruit showed no apparent effects of apple scab fungus without the benefit of any chemical spray treatment, while neighboring apple trees were considerably infected with apple scab.

Further study and tests of the new seedling and of progeny thereof derived by grafting and also by budding, as performed by me and by others on my behalf and under my control, at Sparta, Mich., Hartford Mich., and elsewhere, convinced me that the new seedling represents a new and distinct variety, despite the uncertainty of its parentage, as evidenced by the following unique combination of characteristics which are outstanding therein and which distinguish it from all other varieties of which I am aware:

(1) A fruit ripening habit of from 2 to 3 weeks earlier than "McIntosh" (unpatented);

(2) The ability of the fruit to hang exceptionally well on the tree while having a long color retention period, with a consequent long period of suitable picking maturity;

(3) An exceptionally attractive bright red skin color of the fruit on the exposed side, combined with an attractive greenish-yellow ground color, with some streaking at the stem end or more streaking on the lesser colored fruit;

(4) An early and quite white color of the fruit flesh in the picking season, changing to a yellowish-creamy white color as the fruit fully ripens on the tree;

(5) Long storage and shelf life of the fruit; and (6) Excellent resistance of the foliage and fruit to apple scab fungus even without chemical treatment.

The accompanying drawing shows typical specimens of the foliage and fruit of my new variety of apple tree as depicted in color as nearly true as it is reasonably possible to make the same in a color illustration of this character, with the foliage specimens depicting both the upper and under surfaces of the leaves, and the fruit specimens depicting both the exterior and interior details of the fruit, certain of which are shown in longitudinal cross-section, and other specimens being shown in both elevation and in plan, but the heavy bloom on the skin largely overlaying the red color.

The following is a detailed description of my new variety, with color terminology in accordance with Koster's Color Guide except where general color terms of ordinary dictionary significance are obvious:

Locality where grown and observed: Sparta and Hartford, Mich.

Dates of first and last pickings: About August 15 and September 5, respectively.

Tree: Medium size; vigorous; upright; spreading; dense; hardy; productive; regular bearer.

*Trunk.*—Medium stockiness; medium smoothness.

*Branches.*—Medium thickness; smooth; much-branched. Color—brown.

*Lenticels.*—Numerous; medium size.

*Leaves.*—Large; wide; medium length; abruptly pointed; medium thickness. Length—about 3½ inches. Width—about 2¼ inches. Color: upper surface—near Holly Green, Plate 82; under surface—near Reseda, Plate 85. Margin—coarsely serrate. Petiole—long (about 1⅜ inches); medium thickness.

Flowers: Medium earliness, as compared with other varieties; medium size.

*Dates of first and full bloom.*—Averages about May 10 and May 18, respectively.

*Color.*—White.

Fruit:

*Maturity when described.*—Eating hard ripeness (about September 7, i.e., 5 days after harvest).

*Size.*—Variable. Axial diameter—about 2¼ inches. Transverse diameter—about 2⅞ inches.

*Form.*— Uniform; symmetrical; regular; truncate at base; roundish oblong; form similar to "Cortland" variety (unpatented).

*Cavity.*—Flaring toward apex; undulate. Depth—about ⅜ inch. Breadth—about 1 inch. Markings—color—green, but slightly russeted.

*Basin.*—Symmetrical; wide; mammiform.

*Stem.*—Medium caliper; pubescent; bracts wanting. Length—about ⅜ inch.

*Calyx.*—Closed; segments persistent; broadly lanceolate; about ⅛ inch long; separated; ascending; converged from base toward center; both outer and inner surfaces pubescent.

*Skin.*—Thin; tough; waxed. Dots—conspicuous; many; small even; circular; color—fawn; distribution—most numerous toward calyx. Ground color—near Yellowish-Green, Plate 73. Color markings—blushed; bright; color of markings—deep bright and attractive red, coresponding to from Amaranth Red, Plate 43 to Oxblood Red, Plate 25. Bloom—from moderate to heavy. Scarfskin—wanting. General color effect—attractive bright red on exposed side, with some streaking at stem end and more streaking on lesser colored fruit.

*Flesh.*—Juicy. Color—white, tinged with red in cortex near skin vascular bundles and calyx-tube only in well-colored fruit. Texture—firm; fine; melting. Flavor—subacid; sprightly. Aroma—distinct. Quality—good.

*Core.*—Median. Bundle area (longitudinal section)—large; broadly ovate; symmetrical. Halves of area—equal. Bundles—conspicuous; color—green, with reddish tinge. Core lines—clasping; distinct in cross-section. Carpellary area—distinct. Calyx-tube—pubescent; cone-shaped; depth of tube to shoulder—about ⅜ inch. Styles—present; distinct. Stamens—in one distinct whorl. Seed cells—axile; open. Cell walls—thin; tender; length—about ¾ inch; breadth—about ¼ inch. Longitudinal section—narrowly ovate. Cross-section—Narrow.

Seeds: Usually 1 perfect and 1 or 2 imperfect; usually no more than 3 in one cell. Color—brown.

Use: Market; local; dessert.

Keeping quality: Excellent; over 3 months in ordinary storage and up to 7 months or more with eating quality still good.

Resistance to:

*Insects.*—Medium resistance to usual insects to which apple tree varieties are normally subject, as determined by comparison with other varieties grown under the same conditions in the Michigan area.

*Diseases.*—Remarkably good resistance of both foliage said fruit to apple scab fungus, even without chemical spray treatment, as determined by comparison with neighboring trees of other varieties grown in the same Michigan area under the same conditions when the neighboring trees of other varieties showed considerable apple scab infection.

I claim:

1. A new and distinct variety of apple tree, substantially as herein shown and described, characterized particularly as to novelty by the unique combination of a fruit ripening habit of from 2 to 3 weeks earlier than "McIntosh" (unpatented), the ability of the fruit to hang exceptionally well on the tree while having a long color rotention period with a consequent long period of suitable picking maturity. an exceptionally attractive bright red skin color of the fruit on the exposed side, combined with an attractive greenish-yellow ground color, with some streaking at the stem end or more streaking on the lesser colored fruit, an early and quite white color of the fruit flesh in the picking season, changing to a yellowish-creamy white color as the fruit fully ripens on the tree, long storage and shelf life of the fruit and excellent resistance of the foliage and fruit to apple scab fungus even without chemical treatment.

No references cited.

ROBERT E. BAGWILL, *Primary Examiner.*